United States Patent [19]

Abram et al.

[11] Patent Number: 5,266,713
[45] Date of Patent: Nov. 30, 1993

[54] ARYL ALKENOIC ACID DERIVATIVES AS LEUKOTRIENE ANTAGONISTS

[75] Inventors: Trevor S. Abram, Marlow; Peter Norman, Slough; Stephen R. Tudhope, Windsor, all of England; Harold C. Kluender, Trumbull; Robert N. Schut, Orange, both of Conn.; Heinrich Meier; Ulrich Rosentreter, both of Wuppertal, Fed. Rep. of Germany

[73] Assignee: Miles Inc., West Haven, Conn.

[21] Appl. No.: 928,693

[22] Filed: Aug. 12, 1992

Related U.S. Application Data

[63] Continuation of Ser. No. 386,540, Jul. 27, 1989, abandoned.

[51] Int. Cl.$^5$ .................................. C07C 235/00
[52] U.S. Cl. ........................... 554/36; 554/42; 554/101; 554/213; 554/218; 554/219; 554/220; 554/223; 554/85; 554/115; 554/116; 554/121; 560/9; 560/37; 560/55; 560/101; 560/147; 560/155; 560/171; 560/181
[58] Field of Search .................... 554/42, 44, 45, 46, 554/48, 63, 65, 85, 88, 94, 108, 113, 115, 116, 121, 213, 215, 36, 101, 218, 219, 220, 223; 548/250; 560/9, 171, 37, 181, 35, 101, 147, 185

[56] References Cited

U.S. PATENT DOCUMENTS 4,775,662  10/1988  Gleason ..................... 514/19

FOREIGN PATENT DOCUMENTS 296732  12/1988  European Pat. Off.
375348   6/1990  European Pat. Off.

OTHER PUBLICATIONS

Bernstein et al, Journal of Medicinal Chemistry vol. 31, 1988, pp. 692–696.

*Primary Examiner*—José G. Dees
*Assistant Examiner*—Deborah D. Carr
*Attorney, Agent, or Firm*—Mary G. Boguslaski

[57] ABSTRACT

Aryl alkenoic acid derivatives, and physiologically acceptable salts thereof, are provided which are potent leukotriene antagonists and may be used for the treatment of circulatory diseases and preferably for respiratory diseases such as asthma. The derivatives have a general formula I $$\text{(R}^2\text{)}\text{-Ph-T}(CH_2)_n Z\text{-Ph(R}^3)\text{-}(CH_2)_m W\text{-CHCH}(CH_2)_o A \quad \text{with OH and XR substituents} \quad (I)$$

in which
$X$ is —S—,
$W$ is CH=CH;
$o$ is 1 to 4;
$n$ is 2 to 6;
$m$ is 0 to 2;
$T$ and $Z$, same or different, represent oxygen or a direct bond;
$R^2$ and $R^3$, represent hydrogen, or fluorine;
$A$ represents carboxyl, $CO_2R^4$, wherein $R^4$ is lower alkyl
$R$ is $$\text{Ph(R}^{10}\text{)-Y} \quad \text{or} \quad -CH_2-C(R^7)(R^8)-C(=O)R^9$$

wherein
$Y$ represents carboxyl, $CO_2R^4$, wherein $R^4$ is lower alkyl
$R^7$ and $R^8$, same or different, represent H or lower alkyl;
$R^9$ represents —OH, —O-alkyl, $NH_2$ or a $NHCH_2CO_2H$ group; and
$R^{10}$ $R3$ is H.

6 Claims, No Drawings

ARYL ALKENOIC ACID DERIVATIVES AS LEUKOTRIENE ANTAGONISTS

This is a continuation of application Ser. No. 386,540, filed Jul. 27, 1989, now abandoned.

FIELD OF THE INVENTION

The invention relates to aryl alkenoic acid derivatives, processes for their preparation and their use in medicaments. Preferred compounds of this invention are leukotriene antagonists which may be used to treat such diseases as asthma or circulatory disorders.

UTILITY

Leukotrienes, like prostaglandins, are metabolites of the polyunsaturated essential fatty acids. Leukotrienes are generated via the lipoxygenase enzymatic pathway:

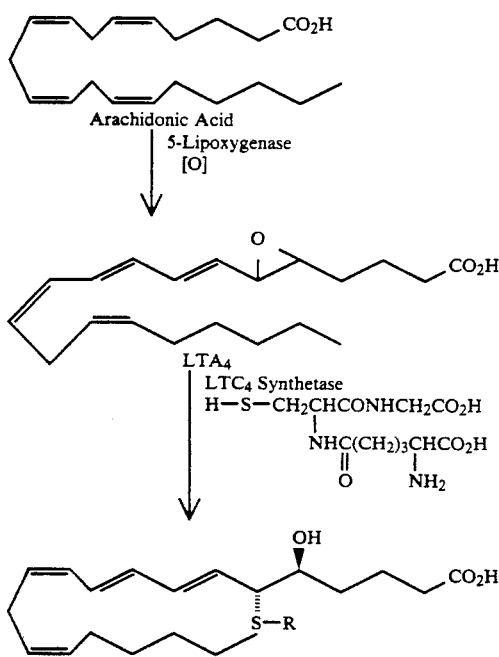

The intermediate $LTA_4$ is a transient species which can be converted in vivo into the peptidoleukotriene $LTC_4$ by attack of the sulfhydryl group of gluathione on the epoxide ring. $LTC_4$ is converted to $LTD_4$ and $LTE_4$ by the sequential action of peptidases.

The peptidoleukotrienes, such as those shown above, have potent actions on pulmonary, vascular and gastrointestinal smooth muscle. In particular the leukotrienes display bronchoconstrictor effects and are believed to play a role in the pathophysiology of asthma. Since bronchoconstrictor effects are considered to be mediated by specific receptors in the lung, one approach to treatment of asthma could be the development of agents which would antagonize the actions of leukotrienes at these receptors. The leukotriene antagonists of this invention can be used to treat asthma since they antagonize the actions of leukotrienes in the lungs and block the bronchoconstrictor effects.

BACKGROUND OF THE INVENTION

There has been a great deal of work done on leukotriene antagonists in recent years. Examplary of the work are European Patent application, publication number 296-732A, and J. Med. Chem., 31, 692–696 (1988). Neither of these citations disclose or suggest the compounds of the invention, which compounds have preferred leukotriene antagonist activity. Each discloses a basic structure which may be varied widely. Compounds of the EP application contains compounds of the basic structure:

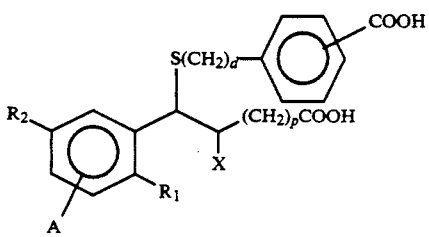

In a preferred species $d=0$ or 1; $p=0$; $A=R_z=H$; $X=H$, OH or $OCH_3$; $R_1=(CH_2)_8$-Phenyl.

The Journal of Medicinal Chemistry article discloses compounds of the general formula

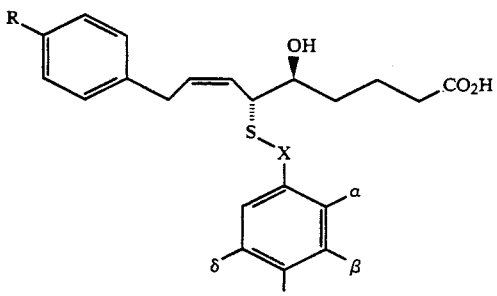

In the most characterized compound $R=C_7H_{15}$; $X=CH_2$; $\alpha=OCH_3; \beta=\delta=H$; and $\gamma=CO_2H$.

SUMMARY OF THE INVENTION

The invention provides aryl alkenoic acid derivatives, and the salts thereof, having the general formula I

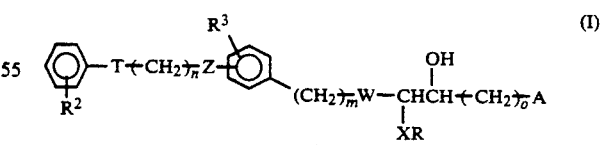

and a process for their preparation. The substituents shown in formula I are defined as X is —S—, —SO—, —SO₂—, or —O—;

W is CH=CH or CH₂—CH₂;

o is 1 to 5;

n is 1 to 10;

m is 0 to 7;

T and Z, same or different, represent oxygen or a direct bond;

$R^2$ and $R^3$, same or different, represent hydrogen, alkyl, alkoxy, halogen, trifluoromethyl, trifluoromethoxy, cyano or nitro groups;

A represents carboxyl, tetrazolyl, $CO_2R_4^4$, $CONR^5R^6$ or nitrile group wherein $R^4$ is lower alkyl and $R^5$ and $R^6$ are H, lower alkyl, alkylsulfonyl, arlysulfonyl or R5 and R6 together are an alkylene chain forming a ring; and R is

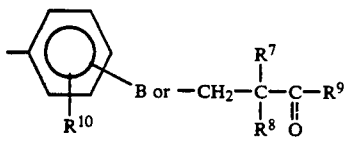

wherein

Y represents carboxyl, tetrazolyl, $CO_2R^4$, $CONR^5R^6$ or nitrile group wherein $R^4$ is lower alkyl and $R^5$ and $R^6$ are H, lower alkyl, alkylsulfonyl, arlysulfonyl or R5 and R6 together are an alkylene chain forming a ring;

$R^7$ and $R^8$, same or different, represent H or lower alkyl;

$R^9$ represents —OH, —O-alkyl, $NH_2$ or a $NHCH_2CO_2H$ group; and $R^{10}$ is H, alkyl, alkoxy, halogen, $CF_3$, $CF_3O$, CN or $NO_2$ These aryl alkenoic acid derivatives having antagonist activity of the response of respiratory tissue to $LTD_4$, $LTC_4$ or $LTE_4$ tests may be used for the therapeutic treatment of diseases of the respiratory system such as asthma. The compounds may be used in medicaments, which generally contain from about 0.5% to 98% by weight of the compound. The medicaments may be used generally for the treatment of diseases of the circulatory and/or respiratory system.

Compounds of formula I may be prepared by a process comprising the steps of:

a. reacting an aldehyde of formula II and a phosphorus compound of formula III in inert solvents in the presence of a base to produce an intermediate compound of formula IV;

wherein the formula II aldehydes have the general structure

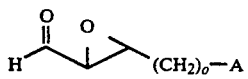
(II)

in which o represents a number 1, 2, 3 or 4; and A represents a carboxyl group or ester thereof;

the formula III phosphorus compounds have the general structure

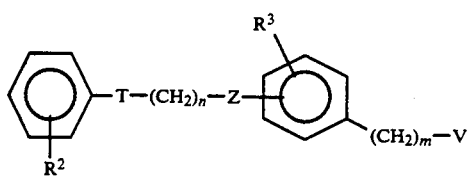
(III)

in which
$R^3$ represents H;
$R^2$ represents H or F;

n represents a number 2, 3, 4, 5 or 6;
m represents a number 0, 1 or 2;
T and Z, same or different, represent oxygen or a direct bond; and
V represents a group of the formulae

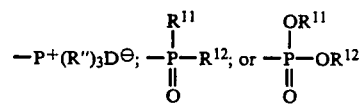

where $R^{11}$ and $R^{12}$, same or different, are alkyl or phenyl; and $D^\ominus$ is a halide anion or tosylate anion;

wherein compounds of formula IV have the general structure

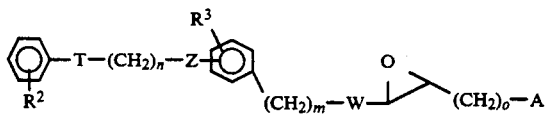

b. reacting compounds having formula IV with mercaptans or alcohols of the formula V in suitable solvents in the presence of trialkylamine bases to produce an compound of formula I;

wherein compounds of formula V have the general structure

H—X—R (V)

in which X is —S— or —O—; and R is

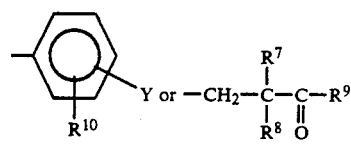

The compound of formula I, when it is prepared as an ester, may optionally be hydrolyzed or partially hydrolyzed in the presence of a base in a mixture of water and a suitable organic solvent. Compounds with X=S can be optionally oxidized with reagents such as hydrogen peroxide, peracids, oxygen, ozone, hypochlorite salts, hydroperoxides, acidic oxidation and the like in suitable solvents such as alcohol, water, acetone or acetonitrile to yield products with X=SO (sulfoxides) or $SO_2$ (sulfones). The reaction steps are commonly carried out in the temperature range from −80° C. to +70° C.

DETAILED DESCRIPTION OF THE INVENTION

General Reaction Scheme

The halogen or sulfonyloxy precursors (1) for the appropriate Wittig reagent are prepared by conventional methods as described in Examples 1 and 2. Compounds of general structure 1 are converted into the corresponding Wittig reagents (2) by reaction with triphenylphosphine and alkyl lithium as described in Examples 3 and 4. Reaction of Wittig reagent 2 with epoxyaldehyde ester 3 gives the epoxy olefin 4 as described in Example 4. The epoxide ring is opened in a regiospecific manner using the appropriate mercapto or hydroxy nucleophile to produce compounds of the present invention (5) (cf. Example 5). Protected ester derivatives may be hydrolyzed to the corresponding free acids by mild alkaline hydrolysis as described in Example 7. Derivatives with X=S can be oxidized by a variety of mild oxidizing agents to yield sulfoxides with X=—SO or sulfones with X=SO₂ using methods well known to one skilled in the art. The compound of structure 3 can be prepared as described by E. J. Corey, et al, *J. Amer. Chem. Soc.*, 102, 1436, (1980).

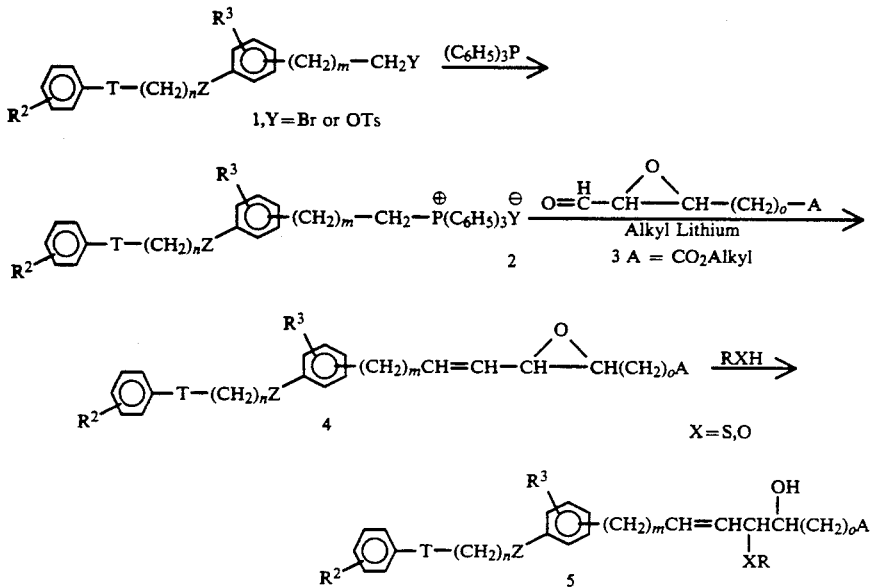

The invention provides aryl alkenoic acid derivatives, and the salts thereof, having the general formula I

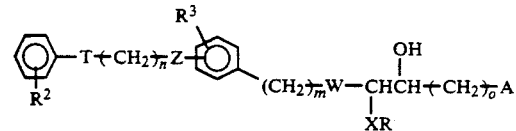

in which
X is —S—, —SO—, —SO₂— or —O—;
W is CH=CH or CH₂—CH₂;
o is 1 to 5;
n is 1 to 10;
m is 0 to 7;
T and Z, same or different, represent oxygen or a direct bond;
$R^2$ and $R^3$, same or different, represent hydrogen, alkyl, alkoxy, halogen, trifluoromethyl, trifluoromethoxy, cyano or nitro groups;
A represents carboxyl, tetrazolyl, $CO_2R_4{}^4$, $CONR^5R^6$ or nitrile group wherein $R^4$ is lower alkyl and $R^5$ and $R^6$ are H, lower alkyl, alkylsulfonyl, arlysulfonyl or R5 and R6 together are an alkylene chain forming a ring; and
R is

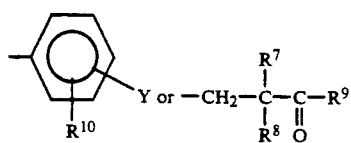

wherein
Y represents carboxyl, tetrazolyl, $CO_2R^4$, $CONR^5R^6$ or nitrile group wherein $R^4$ is lower alkyl and $R^5$ and $R^6$ are H, lower alkyl, alkylsulfonyl, arlysulfonyl or R5 and R6 together are an alkylene chain forming a ring;
$R^7$ and $R^8$, same or different, represent H or lower alkyl;
$R^9$ represents —OH, —O-alkyl, $NH_2$ or a $NHCH_2CO_2H$ group; and
$R^{10}$ is H, alkyl, alkoxy, halogen, $CF_3$, $CF_3O$, CN or $NO_2$ The substances according to the invention are potent leukotriene antagonists and may be used for the therapeutic treatment of humans and animals.

The compounds of formula (I) may also be used in the form of their salts. In general, in this context, the salts are physiologically acceptable and are formed with organic or inorganic bases. The intermediate esters or mixed ester acids or salts thereof may also be used as active compounds in medicaments.

Physiologically acceptable salts are preferred within the scope of the present invention. Physiologically acceptable salts of the aryl alkenoic acid derivatives can be metal or ammonium salts of the substances according to the invention which have free carboxyl groups. Examples of those which are particularly preferred are sodium, potassium, magnesium or calcium salts, as well as ammonium salts which are derived from ammonia or organic amines such as, for example, ethylamine, di- or triethylamine, di- or triethanolamine, dicyclohexylamine, dimethylaminoethanol, arginine or ethylenediamine.

Double bonds can be either cis- or trans-configurated. The carbons at the attachments of X and the hydroxyl group in structure I can be either R- or S-configurated.

In general, alkyl represents straight-chain or a branched hydrocarbon radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkoxy generally represents a straight-chain or branched hydrocarbon radical which has 1 to 12 carbon atoms and is bonded via an oxygen atom. Lower alkoxy having 1 to 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

In general, aryl represents an aromatic radical having 6 to 12 carbon atoms. Preferred aryl radicals are phenyl, naphthyl and biphenyl.

Halogen generally represents fluorine, chlorine, bromine or iodine, preferably fluorine, chlorine or bromine. Halogen particularly preferably represents fluorine or chlorine.

Sulfoxide may be represented by the formula S=O.
Sulfone may be represented by the formula

The compounds of formula I may be prepared by a process characterized in that an aldehyde of the formula II

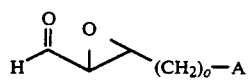

in which o and A have the above mentioned meanings are reacted with phosphorus compounds of the general formula III

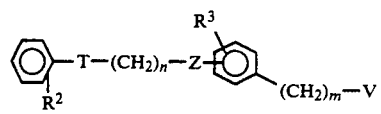

in which $R^2$, T, Z, n, $R^3$ and m have the above mentioned meanings and V represents a group of the formula

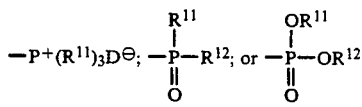

where
$R^{11}$ and $R^{12}$ are identical or different and denote alkyl or phenyl; and
$D^\ominus$ denotes a halide anion or tosylate anion; in inert solvents in the presence of bases to yield intermediate compounds of the formula IV.

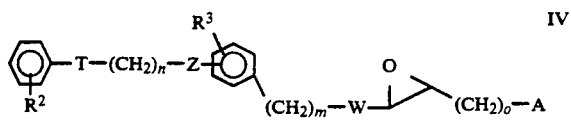

Halide anions of group V are preferably chlorides, bromides or iodides. Suitable inert solvents for the process according to the invention are those conventional organic solvents which do not change under the reaction conditions. They include, but are not limited to, tetrahydrofuran, diethylether, diisopropyl ether, dimethoxyethane, benzene, toluene and hexane or mixtures thereof. Suitable bases include conventional basic compounds, preferably alkali metal hydrides, such as, but not limited to, butyllithium and sodium hydride.

The reactions are generally carried out in the temperature range from −80° C. to +70° C., preferably from about −80° C. to about +20° C. The reaction may be carried out at atmospheric, elevated or reduced pressure, for example 0.5 to 5 bar. Commonly, the reaction is carried out at atmospheric pressure.

When carrying out the reaction the phosphorus compounds are generally employed in an amount of from 1 to 2 moles, preferably in molar amounts, relative to 1 mole of the aldehyde. The bases are generally employed in an amount of from 1 to 5, preferably from 1 to 2 moles, relative to 1 mole of the phosphorus compound.

The process according to the invention can be carried out for example by adding the base and then the aldehyde, if appropriate in a suitable solvent, to the phosphorus compounds dissolved or suspended in a suitable solvent, and if appropriate, heating the mixture. The working up is effected in a conventional manner by extraction, chromatography and/or crystallization.

When carrying out the process according to the invention, it is likewise possible to employ the appropriate phosphoranes [$(R^6)_3P=CHR$], which have previously been prepared from the appropriate phosphonium salts and bases in a separate reaction, directly in place of the phosphonium salts (W=−P($R^6$)$_3{}^\oplus T^\ominus$). However, it has proven favourable to carry out the reaction with the phosphorus compounds in the presence of bases as a one-pot process.

The intermediate compounds of formula IV are then reacted with mercaptans or alcohols of the formula V

 H—X—R      V in which X and R have the above mentioned meanings, in suitable solvents such as methanol or ethanol in the presence of trialkyl amine bases such as triethylamine or diethyl-cyclohexylamine to yield products of formula I. Optionally the resultant esters are hydrolyzed or partially hydrolyzed in the presence of bases such as lithium, sodium or potassium hydroxide in a mixture of water and a suitable organic solvent such as methanol, ethanol, tetrahydrofuran, methylene chloride or paradioxane.

The leukotriene antagonists shown in formula I can also be used as esters, amides and physiologically active salts thereof. Such esters include methyl, ethyl, isopropl, amyl. Esterification may provide a protective function on administration so that upon metabolism to the carboxylic acid, the active component, is released. Physiologically active salts such as sodium or ammonium may provide solubility advantages in formulations such as nasal sprays.

The compounds of the general formula (I) according to the invention have pharmacological properties and in particular they are antagonists for leukotriene diseases; asthma, circulatory diseases, respiratory diseases. They can therefore be used as pharmaceuticals.

The new active compounds can be converted in a known manner into the customary formulations, such as tablets, dragees, pills, granules, aerosols, syrups, emulsions, suspensions and solutions, using inert nontoxic, pharmaceutically suitable excipients or solvents. The therapeutically active compound should in each case be present in a concentration of about 0.5 to 98% preferably 1 to 90%, by weight of the total mixture, that is to say in amounts which suffice to achieve the dosage range indicated.

The formulations are prepared, for example, by extending the active compounds with solvents and/or excipients, optionally with the use of emulsifiers and/or dispersing agents, and, for example, when using water as a diluent, organic solvents can optionally be used as auxiliary solvents.

Examples of auxiliary substances which may be mentioned are: water, non-toxic organic solvents, such as paraffins (for example petroleum fractions), vegetable oils (for example groundnut oil/sesame oil), alcohols (for example ethyl alcohol and glycerol), excipients, such as for example, ground natural mineral (for example kaolins, aluminas, talc and chalk), ground synthetic mineral (for example highly disperse silica and silicates) and sugars (for example sucrose, lactose and glucose), emulsifiers (for example polyoxyethylene fatty acid esters), polyoxyethylene fatty alcohol ethers (for example lignin, suphoite waste liquors, methylcellulose starch and polyvinylpyrrolidone) and lubricants (for example magnesium stearate, talc, stearic acid and sodium sulphate).

Administration is effected in the customary manner, preferably orally, by inhalation or parenterally, particularly perlingually or intravenously. In the case of oral use, the tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants such as magnesium stearate, sodium lauryl sulphate and talc, can be used concomitantly in the production of tablets. In the case of aqueous suspensions, the active compounds can be mixed with various flavor-improving agents or colorants in addition to the abovementioned auxiliary substances.

In the case of parenteral use, solutions of the active compounds, using suitable liquid excipients, can be employed.

In general, it has proved advantageous, in the case of intravenous administration, to administer amounts of about 0.001 to 1 mg/kg, preferable about 0.01 to 0.5 mg/kg, of body weight to achieve effective results, and in the case of oral administration, the dosage is about 0.01 to 20 mg/kg, preferably 0.1 to 10 mg/kg of body weight.

Nevertheless, it may be necessary, under certain circumstances, to deviate from the amounts mentioned, and in particular to do so as a function of the body weight or of the nature of the administration method, of the individual reaction towards the medicament, the nature of its formation, and the time or interval over which the administration takes place. Thus, it can in some cases suffice to use the minimum amount, whereas in other cases the upper limit mentioned must be exceeded. In the case of administration of larger amounts, it may be advisable to divide these into several individual administrations over the course of the day.

Biological Testing

The leukotriene antagonist activity of the compounds of this invention is measured by the ability of the compounds to inhibit the leukotriene induced contraction of guinea pig trachea in vitro.

Spiral strips of guinea pig trachea (male Dunkin-Hartley strain) were bathed in modified Tyrodes buffer, containing 3 μM indomethacin, in jacketed 10 mL tissue baths at 37° C. and continuously aerated with 95% $O_2$/5% $CO_2$. The tissues were connected via cotton sutures to isotonic transducers and they were equilibrated for 60 minutes. 100 μM histamine was added to determine the maximal response of the tissues. Histamine was removed by washout to give a steady baseline. The test compound, or vehicle control, was added cumulatively in half-log units until a bath concentration of 10 μM was reached. After a further equilibration period of 15 minutes, curve of a concentration response to the reference agonist ($LTD_4$ or $LTC_4$) was generated. All determinations were carried out in triplicate and observations normalized against maximal leukotriene response. Least-squares linear regression analysis was then used to calculate the concentration of leukotriene needed to elicit 50% of the maximum response which defined as the $EC_{50}$. The negative logarithm of the antagonist affinity constant ($pK_B$) is then given by the equation:

$$pK_B = 10^{-5}/DR\text{-}1$$

where $$DR = \frac{EC_{50} \text{ (presence of test compound)}}{EC_{50} \text{ (absence of test compound)}}$$

Some antagonist values are shown in the following table:

| Example No. | $pK_B$ (GPT) |
| --- | --- |
| 7-cis | 6.4 |
| 7F-cis | 6.4 |
| 7G-trans | 6.5 |
| 7Q-trans | 8.4 |
| 7R-trans | 8.8 |
| 10-cis | 7.1 |
| 7P-cis | 6.8 |
| 7P-trans | 7.2 |
| 10-trans | 6.6 |

EXAMPLE 1

3-(4-Phenoxybutoxy)benzyl alcohol

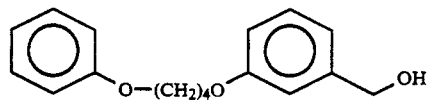

A mixture of 12.4 g (100 mmol) of 3-hydroxybenzyl alcohol (Aldrich), 22.8 g (100 mmol) of 4-phenoxybutyl bromide (Aldrich), 100 mL of isopropyl alcohol and 13.8 g (100 mmol) of pulverized anhydrous potassium carbonate was refluxed under nitrogen for 24 hours. The resultant mixture was evaporated in vacuo to remove most isopropanol, and the product was triturated with water to remove inorganic salts. Yield of title compound was 26.5 g (96%) obtained as a white solid (mp 47°–48° C.).

Analytical Data: NMR ($CDCl_3$, 300 MHz) δ 1.9–2.05 (5 H, m), 3.95–4.1 (4 H, m), 4.62 (2 H, d, J=4.5 Hz), 6.81 (1 H, dd, J=9.8, 3 Hz), 6.85–7.0 (5 H, m) and 7.2–7.32 (3 H, m); TLC ($CHCl_3$) $R_f$ 0.32.

Analogs of Example 1

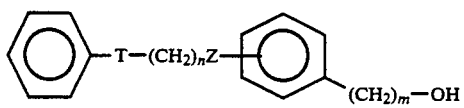

Using the appropriate commercially available substituted phenols and phenyl or phenoxyalkyl bromides and the procedure of Example 1, the following analogs of Example 1 alcohol were formed.

TABLE 1

| Exam. | n | o,m or p | m | Z | T | mp(°C.) | Yield(%) | TLC-$R_f$(Solvent) |
|---|---|---|---|---|---|---|---|---|
| 1A | 4 | p | 2 | 0 | 0 | 102 | 70.5 | 0.43 ($CH_2Cl_2/C_2H_5OH$-97:3) |
| 1B | 3 | p | 3 | 0 | 0 | 56 | 86.9 | 0.53 ($CH_2Cl_2/CH_3OH$-95:5) |
| 1C | 3 | p | 2 | 0 | 0 | 77 | 80.8 | 0.75 ($CH_2Cl_2/CH_3OH$-95:5) |
| 1D | 3 | m | 2 | 0 | 0 | — | 56.6 | 0.44 ($CH_2Cl_2/CH_3OH$-97:3) |
| 1E | 3 | o | 2 | 0 | 0 | — | 89.5 | 0.43 ($CH_2Cl_2/CH_3OH$-97:3) |
| 1F | 4 | p | 1 | 0 | 0 | 106 | 77.0 | 0.31 ($CHCl_3$) |
| 1H | 4 | o | 1 | 0 | 0 | 33–34 | 74.0 | 0.51 ($CHCl_3$) |
| 1I | 5 | p | 1 | 0 | 0 | — | 75.0 | — |
| 1J | 3 | p | 1 | 0 | 0 | 71 | 56.6 | 0.42 ($CH_2Cl_2/CH_3OH$-95:5) |
| 1K | 4 | p | 1 | 0 | $CH_2$ |  | 8.5 |  |
| 1L | 4 | m | 2 | 0 | 0 |  | 83.9 |  |
| 1M | 2 | m | 2 | 0 | 0 |  | 99.0 |  |
| 1N | 3 | m | 2 | 0 | $CH_2$ |  | 51.9 | 0.17 (EtOAc/cyclohexane-2:8) |
| 1O | 4 | o | 1 | 0 | $CH_2$ |  | 35.6 | 0.18 (EtOAc/cyclohexane-2:8) |

EXAMPLE 1P 4-(5-Phenoxypentyl)benzyl alcohol

Step (1)

5-Phenoxypent-1-yne—The process described by the Swiss patent [Chem. Abstr. 93: 167896d] was used. Thus, a mixture of 2.8 g sodium hydride, 5.51 g phenol in 40 mL dry tetrahydrofuran (THF) was stirred at 0° C. under argon until hydrogen evolution ceased. To the resultant solution was added 10 mL dry hexamethylphosphoric triamide (HMPA) followed by a solution containing 5-chloropent-1-yne (4.85 g) in 5 mL THF. The solution was heated at 80° C. for 3 days. The cooled (ambient temperature) mixture was diluted with n-hexane and water. The hexane layer was washed with 2×50 mL portions of water, 1×10 mL 10% potassium carbonate and dried ($MgSO_4$). The evaporated extract was distilled (bp 115°–118° C., 23 mm) to give the title compound (69%) as a colorless oil.

Analytical Data: NMR ($CDCl_3$) δ2.0 (2 H, m), 2.35 (2 H, m), 2.5 (1 H, t), 4.0 (2 H, t, J=6 Hz), 6.8–7.3 (5 H, m, aromatic).

Step (2)

4-(5-Phenoxypent-1-ynyl)benzaldehyde—By the method of C. D. Perchonock, et al., *J. Med. Chem.*, 29, 1442 (1986), 2.0 g 4-bromobenzaldehyde, 2.1 g (0.013 mole) 5-phenoxypent-1-yne, 0.76 g bis (triphenylphosphine) palladium (II) chloride, and 0.10 g copper (I) iodide in 7.0 mL dry triethylamine were stirred under argon for 17 hours. The mixture was diluted with ethyl acetate and washed with 2% $H_2SO_4$, then with water and finally with saturated aqueous NaCl. The resultant dark solution was treated with about 2 g activated carbon powder, dried over $MgSO_4$ and then filtered and evaporated in vacuo. The residue was purified by silica gel column chromatography using 3–6% ethyl acetate in hexane as eluant. The title compound was obtained as a tan solid (2.2 g, 78%).

Analytical Data: NMR ($CDCl_3$) δ5 2.1 (2 H, t, J=6 Hz), 2.2 (2 H, t, J=6 Hz), 4.1 (2 H, t, J=6 Hz), 6.8–7.8 (9 H, m, aromatics), 10.1 (H, s).

Step (3)

4-(5-Phenoxypent-1-ynyl)benzyl alcohol—To a solution of 2.02 g of 4-5-phenoxypent-1-ynyl)benzaldehyde (from step (2) above) in 50 mL ethanol at 0° C. was added 640 mg sodium borohydride. After stirring for 1 hour, then addition of 8 mL water and evaporation of the solvents in vacuo, the residue was diluted with 2% $H_2SO_4$ and ethyl acetate. The organic layer was washed with brine and saturated $NaHCO_3$ and then dried and the solvent evaporated in vacuo to give the title compound (99%).

Analytical Data: NMR ($CDCl_3$) δ5 2.09 (2 H, t), 2.12 (2 H, t), 2.7 (1 H, t), 4.1 (2 H, t, J=6 Hz), 4.6 (2 H, s), 6.8–7.4 (9 H, m, aromatics).

Step (4)

4-(5-Phenoxypentyl)benzyl alcohol—A solution of 2.1 g of 4(5-phenoxypent-1-ynyl)benzyl alcohol from step (3) above) in 100 mL methanol and 130 mg of 5% palladium on carbon was hydrogenated in a Paar Shaker at 18–39 psi. After 1.5 hours, the reaction mixture was filtered and the solvents removed in vacuo to give the title compound [97%] as a white solid.

Analytical Data: NMR ($CDCl_3$) δ1.6 (6 H, m), 2.6 (2 H, bt, J=6 Hz), 3.2 (OH, bs), 3.8 (2 H, t, J=6 Hz), 4.5 (2 H, s), 6.8–7.3 (9 H, m, aromatics).

EXAMPLE 1Q 3-(5-Phenoxypentyl)benzyl alcohol—Using the procedure described for Example 1P, but substituting 3-bromobenzaldehyde in step (2), the title compound was obtained as a white solid.

Analytical Data: NMR ($CDCl_3$) δ1.6 (6 H, m), 2.3 (OH, bs), 2.6 (2 H, t), 3.9 (2 H, t, J=6 Hz), 4.6 (2 H, s), 6.8–7.3 (9 H, m, aromatics).

EXAMPLE 1R 2-(5-Phenoxypentyl)benzyl alcohol—Using the procedure described for Example 1P, but substituting 2-bromobenzaldehyde in step 2), the title compound was obtained.

Analytical Data: NMR ($CDCl_3$) δ1.6 (7 H, m), 2.6 (2 H, t), 3.9 (2 H, t, J=6 Hz), 4.6 (2 H, s), 6.8–7.3 (9 H, m. aromatics).

EXAMPLE 2

3-(4-Phenoxybutoxy)benzyl bromide

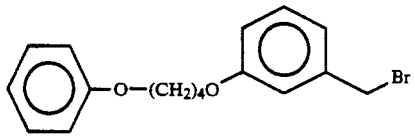

A solution of 10.8 g (40 mmol) of 3-(4-phenoxybutoxy)benzyl alcohol and 17.4 g (53 mmol) of tetrabromomethane in 80 mL of dry dichloromethane was stirred at 15° C. under nitrogen as 13.4 g (52 mmol) of triphenyl phosphine was added portionwise over 30 minutes. The resultant mixture was stirred under nitrogen at ambient temperature for 18 hours and then evaporated in vacuo. The resultant residue was dissolved in minimum chloroform and chromatographed on silica gel using ligroin to fill the column and then 5% ethyl acetate in ligroin to elute the product. The yield of title compound was 9.7 g (72.6%) obtained as a white solid (mp 47°-49°).

Analytical Data: NMR (CDCl$_3$, 300 MHz) δ1.9–2.05 (4 H, m), 3.95=4.1 (4 H, m), 4.45 (2 H, s), 6.82 (1 H, dd, J=9.8, 3 Hz), 6.85–7.0 (5 H, m) and 7.2–7.33 (3 H, m), TLC (EtOAc/Hexane-5:95) R$_f$ 0.33.

Analogs of Example 2

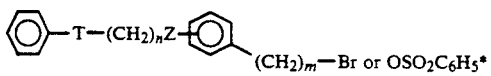

Using the appropriate alcohol and the procedure of Example 2, the following analog bromides were prepared. Tosylates were prepared from the appropriate alcohols and toluenesolfonyl chloride in pyridine at −10° C. to 0° C.

EXAMPLE 3

[3-(4-Phenoxbutoxyl)benzyl]triphenylphosphonium bromide

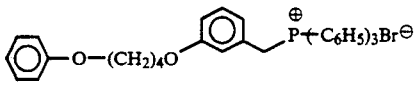

A solution of 6.7 g (20 mmol) of 3-(4-phenoxybutoxy)benzyl bromide and 5.8 g (22.2 mmol) of triphenyl phosphine in 60 mL of dry benzene was refluxed under nitrogen for 24 hours and then cooled slowly to room temperature. The product crystals were removed by filtration, washed with a little benzene and dried in vacuo. The yield of title compound was 12 g (100%) obtained as a white solid (mp 127°-128° C.).

Analytical Data: NMR (DMSO-d$_6$, 300 MHz) δ1.7–1.85 (4 H, m), 3.74 (2 H, t, J=5.2 Hz), 3.98 (2 H, t, J=6 Hz), 5.12 (2 H, d, J=15.8 Hz), 6.49 (1 H, bs), 6.60 (1 H, d, J=7.5 Hz), 6.85–6.97 (4 H, m), 7.17 (1 H, t, J=7.9 Hz), 7.30 (2 H, t, J=7.9 Hz), and 7.6–7.95 (15 H, m).

Analogs of Example 3

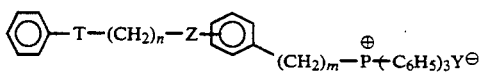

Analogs of Example 3 were produced using the following modified procedure. The appropriate bromide or tosylate was mixed with 1 to 1.1 equivalents of triphenyl phosphine and refluxed in the indicated solvent for the indicated time under nitrogen or argon and then cooled slowly. In some cases, solvent was removed in vacuo (1.0 equivalent triphenyl phospine used) and the residue was used without purification (Example A, B, C, D$^2$). In other cases, the product crystallized from the cooled reaction mixture. It was collected by filtration, washed with a little cold solvent, and dried in vacuo. (Example Q, F, J). In yet other cases, the product settled as an oil. This oil was chromatographed on silica gel using CH$_2$Cl$_2$ to elute starting materials and up to 25% CH$_3$OH in CH$_2$Cl$_2$ to elute the product which was then dried in vacuo (Examples P, D$^1$, H, K, L, M, N, O, R).

TABLE 2

| Exam. | n | o,m or p | m | Z | T | mp(°C.) | Yield(%) | TLC-R$_f$(Solvent) |
|---|---|---|---|---|---|---|---|---|
| 2A* | 4 | p | 2 | 0 | 0 | 108 | 84 | 0.55 (CH$_2$Cl$_2$) |
| 2B* | 3 | p | 3 | 0 | 0 | — | 83 | 0.57 (CH$_2$Cl$_2$) |
| 2C* | 3 | p | 2 | 0 | 0 | — | 99 | 0.57 (CH$_2$Cl$_2$) |
| 2D | 3 | m | 2 | 0 | 0 | — | 94 | 0.19 (EtOAc/Hexane-5:95) |
| 2E* | 3 | o | 2 | 0 | 0 | — | 89 | 0.62 (CH$_2$Cl$_2$) |
| 2F | 4 | p | 1 | 0 | 0 | 49–50 | 88 | 0.32 (EtOAc/Hexane-5:95) |
| 2H | 4 | o | 1 | 0 | 0 | 68–70 | 84 | 0.37 (EtOAc/Hexane-5:95) |
| 2J | 3 | p | 1 | 0 | 0 | — | 93 | — |
| 2K | 4 | p | 1 | 0 | CH$_2$ | — | 98 | 0.60 (CH$_2$Cl$_2$:CH$_3$OH-95:5) |
| 2L | 4 | m | 2 | 0 | 0 | — | 100 | — |
| 2M | 2 | m | 2 | 0 | 0 | — | 71.7 | — |
| 2N | 3 | m | 2 | 0 | CH$_2$ | — | 75.1 | 0.40 (EtOAc/Hexane-3:97) |
| 2O | 4 | o | 1 | 0 | CH$_2$ | — | 91.8 | 0.56 (EtOAc/Hexane-5:95) |
| 2P | 4 | p | 1 | CH$_2$ | 0 | — | 59 | 0.33 (EtOAc/Hexane-5:95) |
| 2Q | 4 | m | 1 | CH$_2$ | 0 | — | 78 | 0.32 (EtOAc/Hexane-5:95) |
| 2R | 4 | o | 1 | CH$_2$ | 0 | — | 94.1 | 0.80 (EtOAc/Hexane-2:3) |

*Those examples with (*) in example number are tosylates; all others are bromides.

TABLE 3

| Exam. | n | o,m, or p | m | Z | T | mp(°C.) | Yield | Y | Solvent/Time (hr) |
|---|---|---|---|---|---|---|---|---|---|
| 3A | 4 | p | 2 | 0 | 0 | — | 99 | Tos | Acetonitrile/96 |
| 3B | 3 | p | 3 | 0 | 0 | — | 100 | Tos | Acetonitrile/65 |
| 3C | 3 | p | 2 | 0 | 0 | — | 100 | Tos | Acetonitrile/72 |
| 3D[1] | 3 | m | 2 | 0 | 0 | — | 93 | Br | EtOH/48 |
| 3D[2] | 3 | m | 2 | 0 | 0 | — | 100 | Tos | Acetonitrile/168 |
| 3E | 3 | o | 2 | 0 | 0 | — | 100 | Tos | Acetonitrile/240 |
| 3F | 4 | p | 1 | 0 | 0 | 55 | 65 | Br | Benzene/24 |
| 3H | 4 | o | 1 | 0 | 0 | 152 | 31 | Br | Benzene/24 |
| 3J | 3 | p | 1 | 0 | 0 | — | 70 | Br | Benzene/24 |
| 3K | 4 | p | 1 | 0 | $CH_2$ | — | 68.6 | Br | Benzene/5 |
| 3L | 4 | m | 2 | 0 | 0 | — | 73.6 | Br | EtOH/24 |
| 3M | 2 | m | 2 | 0 | 0 | — | 54.1 | Br | EtOH/24 |
| 3N | 3 | m | 2 | 0 | $CH_2$ | — | 46.2 | Br | EtOH/24 |
| 3O | 4 | o | 1 | 0 | $CH_2$ | — | 52.1 | Br | EtOH/3 |
| 3P | 4 | p | 1 | $CH_2$ | 0 | 201–202 | 88 | Br | Benzene/15 |
| 3Q | 4 | m | 1 | $CH_2$ | 0 | 151 | 100 | Br | Benzene/75 |
| 3R | 4 | o | 1 | $CH_2$ | 0 | — | 71.1 | Br | Benzene/24 |

EXAMPLE 4

Methyl 5S,6S-Epoxy-8-[3-(4-phenoxbutoxy)phenyl]-oct-7Z-enoate and 7E isomer

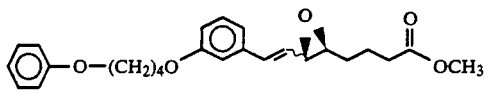

Method A

A slurry of 1.44 g (2.4 mmol) of [3-(4-phenoxy)benzyl]triphenylphosphonium bromide in 40 mL of anhydrous THF was stirred at −25° C. under argon as 1.41 mL (2.2 mmol) of a solution of n-butyllithium in hexane (1.56M) was added dropwise quickly. After 30 minutes stirring at −20° to −25° C. the resultant orange solution was cooled to −70° C. and a solution of 0.34 g (2.0 mmol) of methyl 6-formyl-5S,6R-oxidohexanoate [E. J. Corey, et al., *J. Amer. Chem. Soc.*, 102, 1436 (1980)] in 4 mL dry THF was added dropwise quickly. The resultant yellow solution was stirred 30 minutes at −70° and then allowed to come to 0° and then stirred 1 hour at 0°. The resultant solution was diluted with hexane/ether (1:1) containing 0.5% triethylamine and then washed twice with water. It was then dried over sodium sulfate and evaporated in vacuo. The residue was chromatographed rapidly on silica gel 60 (0.040–0.063 mm) using 40:60 ether/hexane to yield some pure early eluting isomer (Z, cis) and mixed fractions of Z and E product. The mixed product was rechromatographed using 30:70 ether/hexane to yield additional pure cis and pure trans isomer (E, slower eluting). The yield of Z isomer was 280 mg (34%) as a clear oil and the yield of E isomer was 100 mg (12%) as a clear oil.

Analytical Data:

Z (cis) Isomer: TLC $R_f$ 0.38 (1:1-ether/hexane+0.5% triethylamine); NMR ($CDCl_3$, 250 MHz) δ1.5–1.9 (4 H, m), 1.95–2.05 (4 H, m), 2.40 (2 H, t, J=7.8), 2.93–3.00 (1 H, m), 3.54 (1 H, dd, J=7.5, 3.8), 3.68 (3 H, S), 4.0–4.1 (4 H, m), 5.37 (1 H, dd, J=11.2, 8.8), 6.71 (1 H, d, J=11.2), 6.8–7.0 (6 H, m) and 7.24–7.34 (3 H, m).

E (trans) Isomer: TLC $R_f$ 0.33 (1:1-ether/hexane+0.5% triethylamine); NMR ($CDCl_3$, 200 MHz) δ1.5–1.9 (4 H, m), 1.94–2.04 (4 H, m), 2.40 (2 H, t, J=7.3), 2.99–3.0 (1 H, m), 3.27 (1 H, dd, J=8.5, 2), 3.68 (3 H, s), 4.0–4.1 (4 H, m), 5.89 (1 H, dd, J=15.5, 8), 6.72 (1 H, d, J=15.5), 6.74–7.0 (6 H, m) and 7.15–7.34 (3 H, m).

Method B

A solution of 1.2 g (2.0 mmol) of the alkyl phosphonium bromide salt in 30 mL of anhydrous dimethoxyethane was stirred at room temperature under nitrogen as 0.1 g (3.3 mmol) of sodium hydride (80% in mineral oil) was added in several portions. The resultant mixture was heated to 50° for 30 minutes and then recooled to ambient temperature before a solution of 350 mg (2.0 mmol) of oxidoaldehyde in 2 mL dry dimethoxyethane was added dropwise. After 30 minutes at ambient temperature and then 30 minutes at 50°, the product was isolated as in Method A (hexane:ether dilution, etc.). The yield after quick chromatography was 400 mg (49%) of a mixture of the two isomers as a clear oil which could be used without isomer separation until after the next reaction with the appropriate mercaptan. The NMR and TLC data of this mixture are consistent with those of the product produced by Method A.

Analogs of Example 4

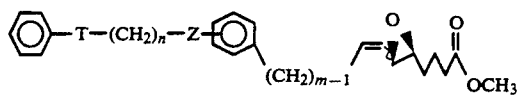

Using the appropropriate phosphonium (Wittig) salt with methyl 6-formyl-5S,6R-epoxyhexanoate [E. J. Coret, et al., *J. Amer. Chem. Soc.*, 102. 1436 (1980)] and the procedure of Example 4 (Method A), the following analog epoxides were prepared.

TABLE 4

| Exam. | n | o,m, or p | m | Z | T | cis Yield | trans Yield | TLC (or mp) |
|---|---|---|---|---|---|---|---|---|
| 4A | 4 | p | 2 | 0 | 0 | 57.5 | — | mp 72.5° C. |
| 4D | 3 | m | 2 | 0 | 0 | 70.6 | — | 0.36 (Ether/Hexane 4:6) |
| 4E | 3 | o | 2 | 0 | 0 | 68.2 | — | 0.55 (Ether/Hexane 4:6) |
| 4F | 4 | p | 1 | 0 | 0 | 13 | 13 | (0.39/0.39 Ether/Hexane 1:1) |
| 4H | 4 | o | 1 | 0 | 0 | 13 | tr | 0.25 (Ether/Hexane 3:7) |

TABLE 4-continued

| Exam. | n | o,m, or p | m | Z | T | cis Yield | trans Yield | TLC (or mp) |
|---|---|---|---|---|---|---|---|---|
| 4J | 3 | p | 1 | O | 0 | 13 | tr | 0.37 (Ether/Hexane 1:1) |
| 4P | 4 | p | 1 | CH$_2$ | 0 | 49.4 | 15.3 | 0.21 (cis (EtOAc/Hexane 0.17 trans 15:85) |
| 4Q | 4 | m | 1 | CH$_2$ | 0 | 43.4 | 22.2 | 0.18 (cis (EtOAc/Hexane 0.15 trans 15:85) |
| 4R | 4 | o | 1 | CH$_2$ | 0 | 41.8 | 26.7 | 0.45 (cis (EtOAc/Hexane 0.42 trans 4:6) |

NMR—Example A—cis (CDCl$_3$, 300 MHz) δ1.5–2.1 (8H, m), 2.39 (2H, t, J=7Hz), 2.87 (1 H, ddd, J=8, 5, 2Hz), 3.4–3.6 (3H, m), 3.67 (3H, s), 5.16 (1 H, dd, J = 11, 9Hz), 5.85 (1 H, dt, J=11, 8Hz), and 6.8–7.3 ppm (9H, m).

NMR—Example D—cis (CDCl$_3$, 300 MHz) δ1.55–1.9 (4 H, m), 2.27 (2 H, pentet, J=6.0), 2.38 (2 H, t, J=7.9), 2.85–2.92 (1 H, m), 3.4–3.65 (3 H, m), 3.68 (3 H, s), 4.17 (4 H, t, J=6.8), 5.18 (1 H, t, J=11), 5.86 (1 H, dt, J=11, 8), 6.73–6.83 (3 H, m), 6.88–6.98 (3 H, m) and 7.17–7.33 (3 H, m).

NMR—Example E—cis (CDCl$_3$, 300 MHz) δ1.5–1.9 (4 H, m), 2.30 (2 H, pentent, J=6.0), 2.37 (2 H, t, J =7.9), 2.8–2.87 (1 H, m), 3.45–3.67 (3 H, m), 3.67 (3 H, s), 4.15–4.24 (4 H, m), 5.12 (1 H, t, J=11), 5.85 (1 H, dt, J=11, 7.5), 6.85–6.98 (5 H, m) and 7.14–7.34 (4 H, m).

NMR—Example F—cis (CDCl$_3$, 300 MHz)δ1.5–1.95 (4 H, m), 1.95–2.05 (4 H, m), 2.3–2.45 (2 H, m), 2.93–3.0 (1 H, m), 3.53 (1 H, dd, J=9.5, 2.2), 3.68 (3 H, s), 4.0–4.1 (4 H, m), 5.28 (1 H, dd, J=12, 9), 6.67 (1 H, d, J=12), 6.8–6.98 (5 H, m), and 7.23–7.33 (4 H, m).

NMR—Example H—cis (CDCl$_3$, 300 MHz)δ1.5–1.9 (4 H, m), 1.95–2.06 (4 H, m), 2.37 (2 H, t, J=7.5), 2.93–2.98 (1 H, m), 3.46 (1 H, dd, J=8, 2), 3.67 (3 H, s), 4.0–4.1 (4 H, m), 5.35 (1 H, dd, J=12, 9.8), 6.85–7.0 (6 H, m) and 7.23–7.35 (4 H, m).

NMR—Example J—cis (CDCl$_3$, 300 MHz)δ1.5–2.0 (4 H, m), 2.28 (2 H, pentent, J=6.4), 2.40 (2 H, t, J =7.5), 2.92–2.98 (1 H, m), 3.50 (1 H, dd, J=7.5, 2), 3.67 (3 H, s), 4.13–4.23 (4 H, m), 5.29 (1 H, dd, J=11, 7.5), 6.67 (1 H, d, J=11), 6.85–6.99 (5 H, m) and 7.2–7.33 (4 H, m).

NMR—Example P—cis (CDCl$_3$, 60 MHz)δ1.5–2.0 (10 H, m), 2.3–2.8 (4 H, m), 3.0 (1 H, m), 3.5 (1 H, dd, J=8, 2), 3.65 (3 H, s), 3.95 (2 H, t, J=6), 5.35 (1 H, dd, J=11, 8), 6.75 (1 H, d, J=11), 6.9–7.3 (9 H, m).

NMR—Example P—trans CDCl$_3$, 60 MHz)δ1.5–2.0 (10 H, m), 2.3–2.8 (4 H, m), 2.95 (1 H, m), 3.25 (1 H, dd, J=8, 2), 3.65 (3 H, s), 3.95 (2 H, t, J=6), 5.85 (1 H, dd, J=16, 8), 6.75 (1 H, d, J=16), 6.8–7.4 (9 H, m).

NMR—Example R—cis+trans (60:40) (CDCl$_3$, 300 MHz)δ1.5–1.9 (10 H, m), 2.33–3.47 (2 H, m), 2.62–2.77 (2 H, m), 2.92–2.99 (1 H, m), 3.28–3.35 (1 H, m), 3.67 (3 H, s, cis ester), 3.69 (3 H, s, trans ester), 3.92–4.0 (2 H, m), 5.4 (1 H, dd, J=8, 11-cis), 5.81 (1 H, dd, J=7.5, 16-trans), 6.84–6.97 (10 H, m).

EXAMPLE 5

Methyl 5S-Hydroxy-6R-(4-methoxycarbonylphenylthio)-8-[3-(4-phenoxybutoxy)phenyl]oct-7Z-enoate

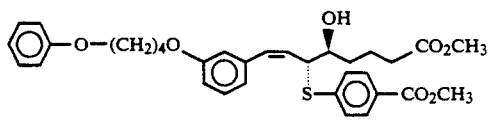

Step 1

Methyl 4-mercaptobenzoate

Commercially available bis-(4-carboxyphenyl) disulfide was esterified to give bis-(4-carbomethoxyphenyl) disulfide as a white solid [m.p. (uncorrected) 133°–135° C.). To 670 mg of bis-(4-carbomethoxyphenyl) disulfide in 45 mL acetic acid, was added, under argon, 654 mg of zinc dust. The mixture was refluxed for 1.5 hours, cooled to ambient temperature and diluted with 50 mL water. The mixture was vacuum filtered and the filtrate purged sequentially for 10 minutes (each) with a stream of argon, hydrogen sulfide and argon. The mixture was diluted with 75 mL ethyl acetate and vacuum filtered through a sintered glass funnel containing Celite ®. The layers of the filtrate were separated and the organic layer dried (MgSO$_4$). The organic extract was evaporated in-vacuo, the residue diluted with toluene and the acetic acid removed by distillation of the toluene-acetic acid azeotrope to give title compound (78%) as a white solid.

Analytical Data:

NMR (DMSO-d$_6$)δ: 3.5 (1 H, bs), 3.9 (3 H, s), 7.5 (2 H, d, aromatics, J=8 Hz), 7.9 (2 H, d, aromatics, J=8 Hz).

Step 2

A solution of 150 mg (0.365 mmol) of methyl 5S,6S-epoxy-8-[3-(4-phenoxybutoxy)phenyl]-oct-7Z-enoate and its 7E isomer (ca. 4:1, Prepared by Method B), 92 mg (0.548 mmol) of methyl 4-mercaptobenzoate and 0.37 mL of triethylamine in 0.7 mL of methanol was stirred under argon at ambient temperature for 1 hour. The resultant solution was diluted with ethyl acetate, washed with 2N sulfuric acid, saturated brine and then dried over sodium sulfate and evaporated in vacuo to yield 340 mg of residue containing the title compound and its 7E isomer. This was chromatographed on silica gel 60 (0.040–0.063 mm) using 45:55-hexane/ether to yield 110 mg (52%) of the pure title compound as a colorless oil and 70 mg (33%) of a mixture of the two isomers.

Analytical Data:

Title Z (cis) Isomer: TLC R$_f$0.18 (hexane/ether-4:6); NMR (CDCl$_3$, 300 MHz)δ1.5–1.9 (4 H, m), 1.9–2.0 (4

H, m), 2.32 (2 H, t, J=7, 5), 2.43 (1 H, d, J=4.5, OH), 3.65 (3 H, s), 3.68-3.78 (1 H, m), 3.89 (3 H, s), 3.9-4.07 (4 H, m), 4.45 (1 H, dd, J=10.1, 4.5), 5.75 (1 H, t, J=11, 6), 6.67 (1 H, d, J=11.6), 6.8-6.97 (6 H, m), 7.2-7.3 (5 H, m) and 7.86 (2 H, d, J=8.3).

E (trans) Isomer: TLC $R_f$ 0.15 (hexane/ether-4:6); NMR (CDCl$_3$, 300 MHz, extra double bond signals attributable to trans isomer)δ6.22 (1 H, dd, J=15.8, 9) and 6.47 (1 H, d, J=15.8).

Analogs of Example 5

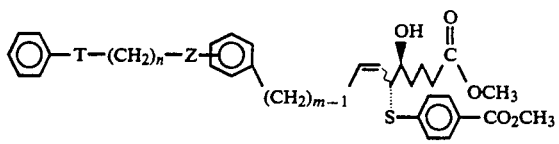

Using the appropriate epoxy analog of Example 4 and the procedure of Example 5, the following mercaptobenzoate analogs were prepared.

TABLE 5

| Exam. | n | o,m or p | m | Z | T | Yield cis | TLC cis | Yield trans | TLC trans | |
|---|---|---|---|---|---|---|---|---|---|---|
| 5A | 4 | p | 2 | 0 | 0 | 55 | — | — | — | (mp 68.5° C.) |
| 5D | 3 | m | 2 | 0 | 0 | 71 | 0.23 | — | — | (Ether/Hexane 6:4) |
| 5E | 3 | o | 2 | 0 | 0 | 64 | 0.24 | — | — | (Ether/Hexane 6:4) |
| 5F | 4 | p | 1 | 0 | 0 | 27 | 0.22 | 27 | 0.17 | (Ether/Hexane 6:4) |
| 5H | 4 | o | 1 | 0 | 0 | 64 | 0.14 | 14 | 0.12 | (Ether/Hexane 6:4) |
| 5P | 4 | p | 1 | CH$_2$ | 0 | 90.1 | * | 51.3 | * | |
| 5Q | 4 | m | 1 | CH$_2$ | 0 | — | — | 62.4 | 0.29 | (Ethyl Acetate 4:6) |
| 5R | 4 | o | 1 | CH$_2$ | 0 | 42 | 0.21 | 21 | 0.17 | (Ether/Hexane 1:1) |

*HPLC - Two Whatman Magnum 950 Silica, 9.9 mL/min EtOAc/Hexane (35:65), cis 11.50 min, trans 12.42 min.

NMR—Example A—(CDCl$_3$, 300 MHz)δ1.39 (3H, t, J=7Hz), 1.5-1.9 (4H, m), 1.95 (4H, mc) 2.25-2.4 (3H, m), 3.31 (2H, bd, J=7Hz), 3.66 (3H, s), 3.72 (1H, mc), 4.01 (4H, mc), 4.24 (1H, dd, J=10, 4Hz), 4.37 (2H, q, J=7Hz), 5.59 (1H, bt, J=10-11 Hz), 5.79 (1H, dt, J=11, 7Hz) and 6.75-7.95 (13H, m).

NMR—Example D—(CDCl$_3$, 300 MHz)δ1.5-1.9 (4 H, m), 2.26 (2 H, pentent, J=6.6), 2.32 (2 H, t, J=6), 3.35 (2 H, d, J=7.5), 3.66 (3 H, s), 3.7-3.78 (1 H, m), 3.92 (3 H, s), 4.14 (2 H, t, J=6.6), 4.15 (2 H, t, J=6.6), 4.25 (1 H, dd, J=10.5, 4.5), 5.62 (1 H, t, J=10.5), 5.83 (1 H, dt, J=10.5, 7.5), 6.66-6.78 (3 H, m), 6.87-7.0 (3 H, m), 7.17 (1 H, t, J=8.25), 7.24-7.33 (2 H, m), 7.44 (2 H, d, J=8.25) and 7.92 (2 H, d, J=8.25).

NMR—Example E—(CDCl$_3$, 300 MHz)δ1.5-1.9 (4 H, m), 2.2-2.35 (4 H, m), 3.27-3.47 (2 H, m), 3.66 (3 H, s), 3.65-3.73 (1 H, m), 3.92 (3 H, s), 4.15 (2 H, t, J=6.6), 4.17 (2 H, t, J=6.6), 4.28 (1 H, dd, J=10, 4), 5.56 (1 H, t, J=11), 5.85 (1 H, dt, J=11, 7.5), 6.8-7.05 (6 H, m) 7.17 (1 H, t, J=8.25), 7.27 (2 H, t, J=7.9), 7.42 (2 H, d, J=8.25) and 7.90 (2 H, d, J=8.25).

NMR—Example F—cis (CDCl$_3$, 300 MHz)δ1.5-1.9 (4 H, m), 1.95-2.05 (4 H, m), 2.32 (2 H, t, J=7.5), 2.43 (1 H, d, J=4, OH), 3.64 (3 H, s), 3.68-3.78 (1 H, m), 3.90 (3 H, s), 4.0-4.1 (4 H, m), 4.45 (1 H, dd, J=12, 4), 5.65 (1 H, t, J=11), 6.64 (1 H, d, J=11), 6.84-6.98 (5 H, m), 7.22-7.32 (6 H, m), and 7.86 (2 H, d, J=7.5).

NMR—Example H—cis (CDCl$_3$, 300 MHz)δ1.5-1.9 (4 H, m), 1.9-1.98 (4 H, m), 2.31 (2 H, t, J=7.5), 2.42 (1 H, d, J=4, OH), 3.65 (3 H, s), 3.67-3.77 (1 H, m), 3.89 (3 H, s), 3.92-4.06 (4 H, m), 4.36 (1 H, dd, J=11, 4), 5.70 (1 H, t, J=11), 6.75 (1 H, d, J=11), 6.84-6.98 (5 H, m), 7.17-7.34 (6 H, m), and 7.81 (2 H, d, J=7.5).

NMR—Example H—trans (CDCl$_3$, 300 MHz)δ1.5-1.94 (4 H, m), 1.94-2.04 (4 H, m), 2.35 (2 H, t, J=7.5), 3.64 (3 H, s), 3.87 (3 H, s), 3.7-4.2 (6 H, m), 6.27 (1 H, dd, J=15, 7.5), 6.8-7.0 (6 H, m), 7.15-7.5 (6 H, m), and 7.82 (2 H, d, J=7.5).

NMR—Example P—trans (CDCl$_3$, 300 MHz)δ1.5-1.85 (10 H, m), 2.29 (OH, d, J=4.6 Hz), 2.33 (2 H, t), 2.62 (2 H, t), 3.65 (3 H, s), 3.85 (1 H, m), 3.9 (3 H, s), 3.94 (2 H, t, J=6.5), 4.0 (1 H, dd, J=9, 4.5), 6.17 (1 H, dd, J=16, 9), 6.49 (1 H, d, J=16), 6.9 (3 H, m), 7.12 (2 H, d), 7.25-7.3 (4 H, m), 7.43 (2 H, d), and 7.85 (2 H, d).

NMR—Example P—cis (CDCl$_3$, 300 MHz)δ1.5-1.9 (10 H, m), 2.3 (2 H, t), 2.4 (OH, d, J=4), 2.65 (2 H, t), 3.65 (3 H, s), 3.72 (1 H, m), 3.9 (3 H, s), 3.96 (2 H, t, J=6.5), 4.46 (1 H, dd, J=11, 4.1), 5.7 (1 H, dd, J=11.5, 11), 6.67 (1 H, d, J=11.5), 6.9 (3 H, m), 7.15-7.3 (8 H, m), and 7.85 (2 H, d).

NMR—Example Q—trans (CDCl$_3$, 200 MHz)δ1.4-1.85 (10 H, m), 2.33 (2 H, t, J=7.5), 2.31 (1 H, d, J=7, OH), 2.60 (2 H, t, J=7.5), 3.65 (3 H, s), 3.88 (3 H, s), 3.76-4.05 (4 H, m), 6.22 (1 H, dd, J=15, 9.5), 6.50 (1 H, d, J=15), 6.85-7.35 (9 H, m), 7.43 (2 H, d, J-8.5), and 7.94 (2 H, d, J=8.5).

NMR—Example R—cis (CDCl$_3$, 300 MHz)δ1.4-1.85 (10 H, m), 2.29 (2 H, t, J=6.4), 2.4 (1 H, d, J=4.5, OH), 2.4-2.6 (2 H, m), 3.64 (3 H, s), 3.6-3.7 (1 H, m), 3.88 (3 H, s), 3.93 (2 H, t, J=7.1), 4.28 (1 H, dd, J=12, 4.5), 5.82 (1 H, t, J=11.9), 6.77 (1 H, d, J=12), 6.85-6.97 (3 H, m), 7.13-7.85 (8 H, m) and 7.83 (2 H, d, J=7.5).

NMR—Example R—cis (CDCl$_3$, 300 MHz)δ1.4-1.9 (10 H, m), 2.27 (1 H, d, OH), 2.35 (2 H, t, J=7.0), 2.58 (2 H, t, J=7.5), 3.66 (3 H, s), 3.88 (3 H, s), 3.9 (1 H, m), 3.93 (2 H, t, J=7.5), 4.05 (1 H, dd, J=9, 4.5), 6.12 (1 H, dd, J=15, 9), 6.85-7.0 (3 H, m), 7.1-7.5 (6 H, m), 7.45 (2 H, d, J=7.5) and 7.94 (2 H, d, J=7.5).

EXAMPLE 6

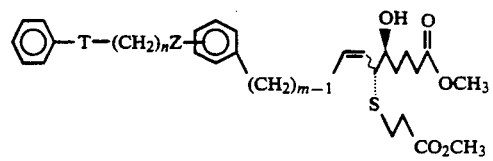

Using the appropriate epoxy analog of Example 4 and methyl 3-mercaptopropionate and the procedure of Example 5, the following mercaptopropionate analogs were prepared.

TABLE 6

| Exam. | n | o,m or p | m | Z | T | Yield cis | TLC cis | Yield trans | TLC trans | |
|---|---|---|---|---|---|---|---|---|---|---|
| 6F | 4 | p | 1 | 0 | 0 | 46.5 | 0.13 | — | — | (Ether/Hexane 1:1) |
| 6G | 4 | m | 1 | 0 | 0 | 46.3 | 0.24 | 61.8 | 0.21 | (Ether/Hexane 6:4) |
| 6H | 4 | o | 1 | 0 | 0 | 30 | 0.13 | 15 | 0.10 | (Ether/Hexane 1:1) |
| 6P | 4 | p | 1 | $CH_2$ | 0 | 84 | * | | | |

*HPLC-Two Whatman Magnum 950 Silica, 9.9 mL/min EtOAc/Hexane (35:65), 13.25 min.

NMR—Example F—cis ($CDCl_3$, 300 MHz)δ1.5–1.9 (4 H, m), 1.95–2.05 (4 H, m), 2.34 (2 H, t, J=7.5), 2.4–2.52 (3 H, m), 2.64–2.84 (2 H, m), 3.67 (3 H, s), 3.68 (3 H, s), 3.67–3.77 (1 H, m), 3.97 (1 H, dd, J=11, 4.5), 4.0–4.1 (4 H, m), 5.57 (1 H, t, J=11), 6.65 (1 H, d, J=11), 6.85–6.98 (5 H, m), and 7.25–7.33 (4 H, m).

NMR—Example G—cis ($CDCl_3$, 300 MHz)δ1.5–1.9 (4 H, m), 1.95–2.05 (4 H, m), 2.34 (2 H, t, J=7.5), 2.4–2.5 (3 H, m), 2.64–2.84 (2 H, m), 3.65 (6 H, s), 3.65–3.76 (1 H, m), 3.96 (1 H, dd, J=11, 4.5), 4.0–4.08 (4 H, m), 5.67 (1 H, t, J=11), 6.68 (1 H, d, J=11), 6.77–7.0 (6 H, m), and 7.2–7.33 (3 H, m).

NMR—Example G—trans ($CDCl_3$, 300 MHz)δ1.5–1.9 (4 H, m), 1.95–2.05 (4 H, m), 2.3 (1 H, d, OH), 2.34 (2 H, t, J=7.5) 2.6 (2 H, t, J=7.5), 2.78 (2 H, t, J=7.5), 3.51 (1 H, dd, J=9, 4.5), 3.66 (3 H, s), 3.68 (3 H, s), 3.73–3.83 (1 H, m), 4.0–4.1 (4 H, m), 6.16 (1 H, dd, J=9, 16), 6.47 (1 H, d, J=16), 6.77–7.02 (6 H, m), and 7.2–7.3 (3 H, m).

NMR—Example H—cis ($CDCl_3$, 300 MHz)δ1.5–1.9 (4 H, m), 1.95–2.0 (4 H, m), 2.3–2.43 (5 H, m), 2.6–2.75 (2 H, m), 3.65 (3 H, s), 3.66 (3 H, s), 3.63–3.73 (1 H, m), 3.82 (1 H, dd, J=9, 4.5), 4.0–4.07 (4 H, m), 5.63 (1 H, t, J=11), 6.77 (1 H, d, J=11), 6.83–6.97 (5 H), and 7.2–7.35 (4 H, m).

NMR—Example P—cis ($CDCl_3$, 300 MHz)δ1.5–1.9 (10 H, m), 2.3 (2 H, t), 2.42 (2 H, t), 2.48 (OH, d), 2.64 (2 H, t), 2.74 (2 H, m), 3.65 (3 H, s), 3.66 (3 H, s), 3.74 (1 H, m), 3.95 (2 H, t, J=6.5), 3.97 (1 H, dd, J=11, 4), 5.63 (1 H, dd, J=11.5, 11), 6.68 (1 H, d, J=11.5), 6.9 (3 H, m), 7.16 (2 H, d), and 7.23–7.3 (4 H, m).

EXAMPLE 7

5S-Hydroxy-6R-[4-carboxyphenylthio]-8-[3-(4-phenoxybutoxy)phenyl]oct-7Z-enoic acid

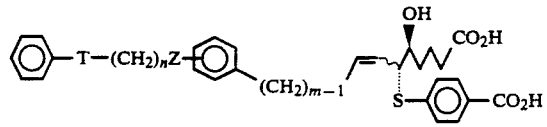

A solution of 110 mg of methyl 5S-hydroxy-6R-(4-methoxycarbonylphenylthio)-8-[3-(4-phenoxybutoxy)-phenyl]oct-7Z-enoate in 7 mL methanol and 1.2 mL of 45% aqueous sodium hydroxide was stirred 3 hours at ambient temperature under argon. The resultant solution was diluted with ice water, acidified to pH3 with 2N sulfuric acid and extracted three times with ethyl acetate. The combined extracts were washed with saturated brine, dried over $Na_2SO_4$ and evaporated in vacuo to leave the title compound as a colorless oil. The yield was 100 mg (95%).

Analytical Data: TLC (System II) $R_f$0.40; NMR (300 MHz, $CDCl_3$)δ1.5–1.9 (4 H, m), 1.9–2.0 (4 H, m), 2.32–2.42 (2 H, m), 3.75–3.85 (1 H, m), 3.9–4.05 (4 H, m), 4.48 (1 H, dd, J=10, 4.5), 4.57 (Trace, Lactone), 5.77 (1 H, t, J=11.5), 6.68 (1 H, d, J=11.5), 6.8–6.95 (6 H, m), 7.2–7.3 (5 H, m), and 7.91 (2 H, d, J=8.3).

Analogs of Example 7

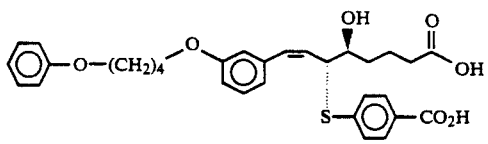

Using the appropriate diester analog and the hydrolysis procedure of Example 7, the following diacid analogs were prepared.

TABLE 7

| Example | n | o,m, or p | m | Z | T | Yield | TLC* |
|---|---|---|---|---|---|---|---|
| 7D-cis | 3 | m | 2 | 0 | 0 | 100 | 0.43 |
| 7E-cis | 3 | o | 2 | 0 | 0 | 99 | 0.45 |
| 7F-cis | 4 | p | 1 | 0 | 0 | 85 | 0.30 |
| 7G-trans | 4 | m | 1 | 0 | 0 | 87 | 0.29 |
| 7H-cis | 4 | o | 1 | 0 | 0 | 79 | 0.39 |
| 7P-cis | 4 | p | 1 | $CH_2$ | 0 | 93 | — |
| 7P-trans | 4 | p | 1 | $CH_2$ | 0 | 94 | — |
| 7Q-trans | 4 | m | 1 | $CH_2$ | 0 | 90 | 0.59 |
| 7R-cis | 4 | o | 1 | $CH_2$ | 0 | 92 | 0.45 |
| 7R-trans | 4 | o | 1 | $CH_2$ | 0 | 88 | 0.45 |

*All TLC with System II - This is the organic (upper) phase from a well shaken mixture of 110 mL of ethyl acetate, 20 mL of acetic acid, 50 mL of 2,2,4-trimethylpentane and 100 mL of water.

NMR—Example D—($CDCl_3$, 300 MHz)δ1.5–2.0 (4 H, m), 2.26 (2 H, pentet, J=6.2), 2.35–2.45 (2 H, m), 3.4 (2 H, d, J=7.5), 3.75–3.83 (1 H, m), 4.13 (2 H, t, J=7.5), 4.15 (2 H, t, J=7.5), 4.30 (1 H, dd, J =9, 2), 5.65 (1 H, t, J=10), 5.87 (1 H, dt, J=10, 7.5), 6.7–6.8 (3 H, m), 6.88–6.98 (3 H, m), 7.18 (1 H, t, J=7.5), 7.27 (2 H, t, J=7.5), 7.44 (2 H, d, J=7.5) and 7.98 (2 H, d, J=7.5).

NMR—Example E—($CDCl_3$, 300 MHz)δ1.5–1.9 (4 H, m), 2.27 (2 H, pentet, J=5.8), 2.32–2.42 (2 H, m), 3.41 (2 H, m), 3.7–3.8 (1 H, m), 4.16 (2 H, t, J=7.5), 4.17 (2 H, t, J=7.5), 4.31 (1 H, dd, J=9.2), 5.57 (1 H, t, J=11) 5.88 (1 H, dt, J=11, 7.5), 6.83–7.3 (9 H, m), 7.41 (2 H, d, J=7.5), and 7.95 (2 H, d, J=7.5).

NMR—Example F—cis ($CDCl_3$, 300 MHz)δ1.5–1.9 (4 H, m), 1.95–2.04 (4 H, m), 2.34–2.44 (2 H, m), 3.74–3.82 (1 H, m), 4.0–4.1 (4 H, m), 4.49 (1 H, dd, J=10, 2), 5.67 (1 H, t, J=11), 6.67 (1 H, d, J=11), 6.8–6.98 (5 H, m), 7.2–7.34 (6 H, m), and 7.92 (2 H, d, J=7.5).

NMR—Example G—trans ($CDCl_3$, 300 MHz)δ1.5–1.9 (4 H, m), 1.95–2.05 (4 H, m), 2.41 (2 H, t, J=7.5), 3.85–3.93 (1 H, m), 3.95–4.1 (5 H, m), 6.23 (1 H, dd, J=16, 10), 6.52 (1 H, d, J=16), 6.75–7.35 (9 H, m), 7.45 (2 H, d, J=7.5), and 7.99 (2 H, d, J=7.5).

NMR—Example H—cis ($CDCl_3$, 300 MHz)δ1.5–2.0 (8 H, m), 2.35 (2 H, t, J=7.5), 3.7–3.8 (1 H, m), 3.8–4.1 (4 H, m), 4.38 (1 H, dd, J=11, 2), 5.72 (1 H, t, J=11), 6.77 (1 H, d, J=11), 6.8–6.98 (5 H, m), 7.1–7.4 (6 H, m), and 7.87 (2 H, d, J=7.5).

NMR—Example R—cis (CDCl₃, 300 MHz)δ1.4–1.85 (10 H, m), 2.3–2.4 (2 H, m) 2.45–2.6 (2 H, m), 3.65–3.75 (2 H, m), 3.93 (2 H, t, J=6.8), 4.3 (1 H, dd, J=10.5, 2), 5.84 (1 H, t, J=11), 6.83 (1 H, d, J=11), 6.85–6.96 (4 H, m), 7.1–7.3 (6 H, m), 7.38 (1 H, d, J=6.8) and 7.89 (2 H, d, J=7.5).

NMR—Example R—trans (CDCl₃, 300 MHz)δ1.4–2.0 (10 H, m), 2.3–2.5 (2 H, m) 2.5–2.8 (2 H, m), 3.5–3.8 (1 H, m), 3.94 (2 H, t, J=7.5), 4.08 (1 H, dd, J=10, 2), 6.13 (1 H, dd, J=16, 9), 6.82 (1 H, d, J=16), 6.82–7.5 (9 H, m), 7.46 (2 H, d, J=7.5), and 7.97 (2 H, d, J=7.5).

EXAMPLE 7A (5S, 6R)-Z-6-(4-carboxyphenylthio)-5-hydroxy-9-[4-(4-phenoxybutoxy)phenyl]-7-nonenoic acid bis sodium salt 0.165 g [0.272 mmol] of (5A) in 5 ml tetrahydrofuran were stirred with two equivalents of 1N sodium hydroxide for several days, monitoring the reaction progress by TLC (silica gel, toluene/ethanol 5:1; R$_f$(free acid)=0.5). Isolation of the bis sodium salt via lyophilization avoided δ-lactonization and gave (III) as a yellowish powder: 0.147 g (89%).

¹H-NMR (D₂O, 300 Mz)δ=1.35–1.75 (m; 8H), 2.05–2.25 (mc; 2H), 3.0–3.2 (m; 2H); 3.76 (s, br; 5H), 4.22 dd, J=10Hz, 3Hz, 1H); 5.4–5.65 [m; 2H); 6.6–7.85 (m; 13Hz).

EXAMPLE 8

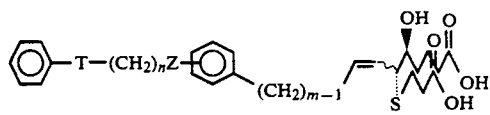

Using the appropriate diester analog and the hydrolysis procedure of Example 7, the following diacid analogs were prepared.

TABLE 8

| Example | n | o,m, or p | m | Z | T | Yield | TLC* |
|---|---|---|---|---|---|---|---|
| 8F-cis | 4 | p | 1 | O | O | 100 | 0.27 |
| 8G-cis | 4 | m | 1 | O | O | 77 | 0.27 |
| 8G-trans | 4 | m | 1 | O | O | 75 | 0.25 |
| 8H-cis | 4 | o | 1 | O | O | 100 | 0.40 |
| 8P-cis | 4 | p | 1 | CH₂ | O | 100 | — |

*All with System II

NMR—Example F—cis (CDCl₃, 300 MHz) δ1.5–1.9 (4 H, m), 1.9–2.05 (4 H, m), 2.3 (2 H, t, J=7.5), 2.42 (2 H, t, J=7.5), 2.5–2.8 (2 H, m), 3.7–3.8 (1 H, m), 3.96 (1 H, dd, J=11, 2), 4.0–4.1 (4 H, m), 5.61 (1 H, t, J=11), 6.62 (1 H, d, J=11), 6.8–7.0 (5 H, m), and 7.2–7.35 (4 H, m).

NMR—Example G—cis (CDCl₃, 300 MHz)δ1.5–1.9 (4 H, m), 1.9–2.05 (4 H, m), 2.38 (2 H, t, J=7.5), 2.47 (2 H, t, J=7.5), 2.6–2.85 (2 H, m), 3.7–3.8 (1 H, m), 4.0 (1 H, dd, J=12, 4), 4.0–4.1 (4 H, m), 5.66 (1 H, t, J=11), 6.7 (1 H, d, J=11), 6.8–7.0 (5 H, m), and 7.2–7.32 (4 H, m).

NMR—Example G—trans (CDCl₃, 300 MHz)δ1.5–2.05 (8 H, m), 2.4 (2 H, t, J=7.5), 2.65 (2 H, t, J=7.5), 2.75–2.85 (2 H, m), 3.5–3.85 (2 H, m), 4.0–4.1 (4 H, m), 6.14 (1 H, dd, J=16, 8), 6.48 (1 H, d, J=16), 6.77–7.0 (5 H, m), and 7.2–7.35 (4 H, m).

NMR—Example H—cis (CDCl₃, 300 MHz)δ1.5–2.05 (8 H, m), 2.38 (2 H, t, J=7.5), 2.6–2.75 (2 H, m), 3.7 (1 H, m), 3.85 (1 H, dd, J=10, 3), 3.95–4.1 (4 H, m), 5.63 (1 H, t, J=11), 6.77 (1 H, d, J=11), 6.8–7.0 (5 H, m), and 7.2–7.35 (4 H, m).

EXAMPLE 9

Methyl 5S-Hydroxy-6R-[2-(N-carbomethoxymethylamine)carbonyl-2,2-dimethyl]ethylthio-8-[4-(5-phenoxypentyl)]-phenyl-7-octenoate Z and E isomers)

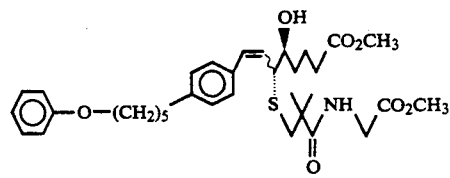

Step (a)

Preparation of 3-Chloro-2,2-dimethylpropanoylglycine

By the method of M. Shimazaki, et al., Chem. Pharm. Bull., 30(9), 3139–3146 (1982), 2.27 g glycine in a solution of 31 mL of 2 M sodium hydroxide was stirred with commercially available chloropivaloyl chloride (4.65 g) in 5 mL ether. After one hour at 0° C., the reaction mixture was warmed to ambient temperature, acidified (pH 2) with sulfuric acid and saturated with sodium chloride. After extraction with 3×30 mL ethyl acetate, the extracts were dried (MgSO₄) and evaporated in vacuo to give 3.0 g of the title compound as a white solid. This material was used as obtained in the following transformation.

Analytical Data: NMR (DMSO-d₆)δ1.2 (6 H, s), 3.7 (2 H, s), 3.8 (2 H, s), 7.9 (2 H, bs). Recrystallized from toluene-hexane. Found C, 43.57; H, 6.13; N, 7.14; C₇H₁₂ClNO₃ requires C, 43.44; H, 6.25, N, 7.24; m.p. [uncorrected] 92°–95° C.

Step (b)

Methyl 3-mercapto-2,2-dimethyl-propanoylglycinate

To a solution containing 2.96 g of 3-chloro-2,2-dimethylpropanoylglycine in 50 mL water was added 4.5 g of commercially available sodium hydrosulfide hydrate. The solution was heated at 80° C. for 16 hours and cooled to ambient temperature. The solution was acidified (pH 2), saturated with salt and extracted with 3×50 mL ether. The combined extracts were dried (MgSO₄), evaporated to a small volume (ca. 10 mL) and cooled to 0° C. To this solution was added, dropwise, an ethereal solution of 0.3M diazomethane until a yellow color persisted (1.1 mole equivalents). The solution was purged with argon and evaporated in vacuo to give a pungent oil. After purification by semipreparative HPLC (2 ×Whatman M-9, partisil® columns, 1:1 v/v hexane-ethyl acetate as eluant, R$_v$=2.43), the title compound was obtained as a white solid. This material was stored under argon at 0° C.

Analytical Data: NMR (CDCl₃)δ1.45 (6 H, s), 1.65 (1 H, t, J=9 Hz), 2.7 (2 H, d, J=9 Hz), 3.76 (3 H, s), 4.05 (2 H, d, J=5 Hz), 6.3 (1 H, bm).

Step (c)

Using the epoxy analog 4P and the mercaptan intermediate from step (b) above and following the procedure of Example 5, the Z and E isomers of Example 9 were produced.

Analytical Data

Z-Isomer: NMR (CDCl$_3$)δ1.20 (3 H, s), 1.21 (3 H, s), 1.4–1.85 (10 H, m), 2.3 (2 H, t), 2.61 (2 H, t), 2.62 (S—CH$_A$, d, J$_{AB}$=12.3 Hz), 2.81 (S—CH$_B$, d, J$_{AB}$=12.3 Hz), 2.83 (OH, d, J=3.5 Hz), 3.65 (3 H, s), 3.74 H$_5$, m), 3.76 (3 H, s), 3.9 (H$_6$, d, J=11.1, 3.5 Hz), 3.95 (—CH$_2$O—, t, J=6.5 Hz), 4.01 (H$_A$H$_B$ of an ABX pattern, J$_{AB}$=21.2 Hz, J$_{AX}$=5.4 Hz, J$_{BX}$=5.3 Hz), 5.65 (H$_7$, dd, J=11.6, 11.1 Hz), 6.32 (NH$_X$ of an ABX pattern), 6.65 (H$_8$, d, J=11.6 Hz), 6.9 (3 H, m, aromatics), 7.15 (2 H, d, aromatics), 7.3 (4 H, m, aromatics); R$_v$ 2.68 (80:20 v/v) acetonitrile-water, C-18, 5 μ, ASI analytical column).

E-Isomer: NMR (CDCl$_3$)δ1.25 (3 H, s), 1.27 (3 H, s), 1.5–1.85 (10 H, m), 2.34 (2 H, t), 2.54 (OH, d, J =4.1 Hz), 2.63 (2 H, t), 2.70 (H$_A$, d, J=12.8 Hz), 2.78 (H$_B$, d, J=12.8 Hz), 3.47 (H$_6$, dd, J=9.7, 4.1 Hz), 3.65 (3 H, s), 3.76 (3 H, s), 3.78 (H$_5$, m), 3.94 CH$_2$OPh, t, J=6.5 Hz), 4.04 (2 H, d, J=5.0 Hz), 6.3 (H$_7$, dd, J=15.8, 9.7 Hz), 6.4 (NH, t), 6.5 H$_8$, d, J=15.8 Hz), 6.9 (3 H, m, aromatics), 7.14 (2 H, d, aromatics), 7.25–7.35 (4 H, m, aromatics): R$_v$ 2.54 (column and eluant as described above for Z-isomer).

EXAMPLE 10

5S-Hydroxy-6R-[2-(N-carboxymethylamino)carbonyl-2,2-dimethyl]ethylthio-8-[4-(5-phenoxypentyl)]phenyl-7-octenoic acid (Z and E isomers)

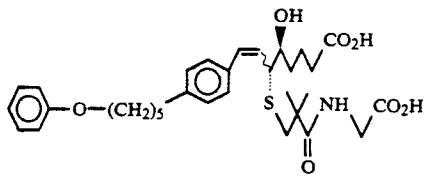

Following the hydrolysis procedure of Example 7, the diesters from Example 9 were converted into the corresponding free acids.

Analytical Data:

Z-Isomer UV (methanol): _246 (ε10,900); R$_v$ 2.60 (65:35 (v/v), pH 7.2 phosphate buffer-acetonitrile, C-18, 5 μ, Whatman partisil 3 RAC, analytical column).

E-Isomer UV (methanol): _265 (ε16,500); R$_v$ 3.14 (column and eluant as described above for Z-isomer).

It is understood that many modifications and variations may be made without departing from the spirit and scope of the invention, which is solely defined by the claims.

What is claimed is:

1. Aryl alkenoic acid derivatives, and the salts thereof, having the general formula I

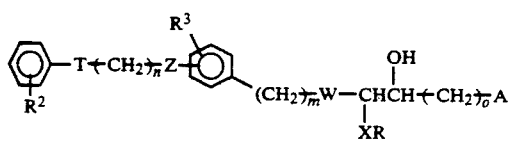

in which
X represents sulfur;
W represents CH=CH;
o represents a number 1, 2, 3, or 4;
n represents a number 2, 3, 4, 5, or 6;
m represents a number 0, 1, or 2;

T and Z, same or different, represent oxygen or a direct bond;
R$^2$ represents hydrogen or fluorine;
A represents carboxyl or an ester thereof and
R is

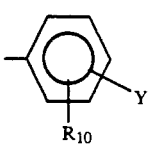

wherein
Y represents carboxyl or an ester thereof;
R$^7$ and R$^8$, same or different, represent H or straight or branched chain lower alkyl having from 1 to about 6 carbon atoms;
R$^9$ represents —OH, —O-alkyl said alkyl representing a straight-chain or branched hydrocarbon radical having 1 to 12 carbon atoms, NH$_2$ or an NHCH$_2$CO$_2$H group; and
R$^{10}$ and R$^3$ represent H.

2. Alkenoic acid derivatives, and their salts, according to claim 1 wherein R is

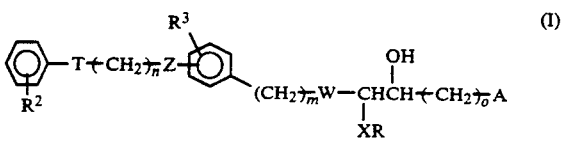

and Y represents a para carboxyl group or an ester thereof.

3. Aryl alkenoic acid derivatives chosen from the group consisting of 5S-hydroxy-6R-4-carboxyphenylthio)-9-[4-(4-phenoxybutoxy)phenyl]-7Z-nonenoic acid bis sodium salt, 5S-hydroxy-6R-(4-carboxyphenylthio)-8-[1-(4-phenoxybutoxy)phenyl]-7Z-octenoic acid, 5S-hydroxy-6R-(4-carboxyphenylthio)-8-[4-(5-phenoxypentyl)phenyl]-7Z-octenoic acid and 5S-hydroxy-6R-(4-carboxyphenylthio)-8-[4-(5-phenoxypentyl)phenyl]-7E-octenoic acid.

4. Aryl alkenoic acid derivatives chosen from the group consisting of 5S-hydroxy-6R-(2-carboxyethylthio)-8-[4-(4-phenoxybutoxy)phenyl]-7Z-octenoic acid and 5S-hydroxy-6R-(2-carboxyethylthio)-8-[4-(5-phenoxypentyl)phenyl]-7Z-octenoic acid.

5. Aryl alkenoic acid derivatives chosen from the group consisting of 5S-hydroxy-6R-(4-aza-5-carboxy-2,2-dimethyl-3-oxopentylthio)-8-[4-(5-phenoxypentyl)-phenyl]-7Z-octenoic and 5S-hydroxy-6R-(4-aza-5-carboxy-2,2-dimethyl-3-oxopentylthio)-8-[4-(5-phenoxypentyl)phenyl]-7E-octenoic acid.

6. Aryl alkenoic acid derivatives, and the salts thereof, having the general formula I

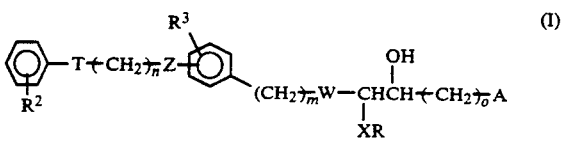

(I)

in which
X is —S—, —SO—, —SO$_2$— or —O—;

W is CH=CH or CH$_2$—CH$_2$;

o is 1 to 5;

n is 1 to 10;

m is 0 to 7;

T and Z, same or different, represent oxygen or a direct bond;

R$^2$ and R$^3$, same or different, represents hydrogen, straight-chain or branched hydrocarbon alkyl radicals having 1 to 12 carbon atoms, straight-chain or branched hydrocarbon alkoxy radical having 1 to 12 carbon atoms and bonded by a oxygen atom, halogen, trifluoromethyl, trifluoromethoxy, cyano or nitro groups;

A represents carboxyl, tetrazolyl, CO$_2$R$^4$, CONR$^5$R$^6$ or nitrile group wherein R$^4$ is straight or branched chain lower alkyl having 1 to about 6 carbon atoms and R$^5$ and R$^6$ are H, straight-chain or branched lower alkyl having 1 to about 6 carbon atoms, alkulsulfonul said alkyl group being a straight-chain or a branched hydrocarbon radical having 1 to 12 carbon atoms, arylsulfonyl said aryl representing an aromatic radical having 6 to 12 carbon atoms or R5 and R6 together are an alkylene chain forming a ring said alkylene chain being defined by R$_5$ and R$_6$ herein; and R is

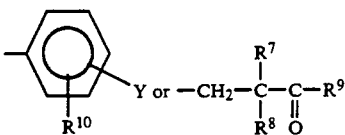

wherein

Y represents carboxyl, tetrazolyl, CO$_2$R$^4$, CONR$^5$R$^6$ or nitrile group wherein R$^4$ is straight or branched chain lower alkyl having 1 to about 6 carbon atoms and R$^5$ and R$^6$ are H, straight-chain or branched lower alkyl having 1 to about 6 carbon atoms, alkulsulfonul said alkyl group being a straight-chain or a branched hydrocarbon radical having 1 to 12 carbon atoms, arylsulfonyl said aryl representing an arcmatic radical having 6 to 12 carbon atoms or R$^5$ and R$^6$ together are an alkylene chain forming a ring said alkylene chain being defined by R$^5$ and R$^6$ herein;

R$^7$ and R$^8$, same or different, represent H or straight-chain or branched lower alkyl having from 1 to about 6 carbon atoms;

R$^9$ represents —OH, —O-alkyl said alkyl represented by straight-chain or branched alkyl groups having 1 to 12 carbon atoms, NH$_2$ or a NHCH$_2$CO$_2$H group; and R$^{10}$ is H, straight-chain or branched alkyl group having 1 to 12 carbon atoms, an alkoxy group represented by a straight-chain or branched hydrocarbon radical which has 1 to 12 carbon atoms and is bonded via an oxygen atom, halogen, CF$_3$, CF$_3$O, CN or NO$_2$.

* * * * *